United States Patent
Bae et al.

(10) Patent No.: US 10,431,506 B2
(45) Date of Patent: Oct. 1, 2019

(54) METHOD OF PROCESSING SUBSTRATE AND METHOD OF FABRICATING SEMICONDUCTOR DEVICE USING THE SAME

(71) Applicant: SAMSUNG ELECTRONICS CO., LTD., Suwon-si (KR)

(72) Inventors: Dusik Bae, Changwon-si (KR); Yoonmi Lee, Seoul (KR); Hyeogki Kim, Hwaseong-si (KR); Kyoungsil Park, Seongnam-si (KR); JungDae Park, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 15/848,896

(22) Filed: Dec. 20, 2017

(65) Prior Publication Data

US 2018/0204777 A1    Jul. 19, 2018

(30) Foreign Application Priority Data

Jan. 17, 2017   (KR) ........................ 10-2017-0008219

(51) Int. Cl.
| | |
|---|---|
| *H01L 21/66* | (2006.01) |
| *H01L 21/311* | (2006.01) |
| *G01N 21/65* | (2006.01) |
| *H01L 21/67* | (2006.01) |
| *H01L 21/033* | (2006.01) |
| *G01N 21/956* | (2006.01) |

(52) U.S. Cl.
CPC ............ *H01L 22/12* (2013.01); *G01N 21/65* (2013.01); *H01L 21/0334* (2013.01); *H01L 21/31116* (2013.01); *H01L 21/67069* (2013.01); *H01L 22/20* (2013.01); *H01L 22/24* (2013.01); *H01L 22/26* (2013.01); *G01N 2021/95676* (2013.01)

(58) Field of Classification Search
None
See application file for complete search history.

(56) References Cited

U.S. PATENT DOCUMENTS

| | | | |
|---|---|---|---|
| 6,225,227 B1 | 5/2001 | Aizawa | |
| 7,301,619 B2 | 11/2007 | Borden et al. | |
| 7,348,190 B2 | 3/2008 | Shin et al. | |
| 8,599,379 B2 | 12/2013 | Sakai et al. | |
| 9,583,358 B2* | 2/2017 | Kim | H01L 21/324 |
| 2005/0037615 A1 | 2/2005 | Cabib et al. | |
| 2006/0019419 A1 | 1/2006 | Shin et al. | |
| 2006/0232768 A1 | 10/2006 | Borden et al. | |

(Continued)

FOREIGN PATENT DOCUMENTS

| | | |
|---|---|---|
| JP | 792237 A | 4/1995 |
| JP | 2518533 B2 | 7/1996 |

(Continued)

*Primary Examiner* — Telly D Green
(74) *Attorney, Agent, or Firm* — Sughrue Mion, PLLC

(57) ABSTRACT

Disclosed are a method of processing a substrate and a method of fabricating a semiconductor device using the same. The method of processing a substrate comprises forming a mask layer on a substrate, inspecting the mask layer, and forming a mask pattern based on an inspection result of the mask layer. The operation of inspecting the mask layer comprises using Raman spectrum analysis to detect defects in the mask layer.

16 Claims, 8 Drawing Sheets

(56) References Cited

U.S. PATENT DOCUMENTS

| | | | |
|---|---|---|---|
| 2010/0025852 A1* | 2/2010 | Ueki | C23C 16/30 |
| | | | 257/761 |
| 2011/0069313 A1 | 3/2011 | Sakai et al. | |
| 2012/0304773 A1 | 12/2012 | Horibe et al. | |
| 2013/0077086 A1 | 3/2013 | Chuang et al. | |
| 2014/0336975 A1 | 11/2014 | Kim et al. | |
| 2015/0025343 A1 | 1/2015 | Gareau et al. | |
| 2015/0348794 A1* | 12/2015 | Kim | H01L 21/324 |
| | | | 438/703 |
| 2017/0040178 A1* | 2/2017 | Kim | H01L 21/324 |
| 2018/0179397 A1* | 6/2018 | Kim | C09D 7/62 |

FOREIGN PATENT DOCUMENTS

| | | |
|---|---|---|
| JP | 10282181 A | 10/1998 |
| JP | 2008235308 A | 10/2008 |
| JP | 2011242248 A | 12/2011 |
| JP | 5178030 B2 | 4/2013 |
| JP | 5522531 B2 | 6/2014 |
| KR | 100711922 B1 | 4/2007 |
| KR | 100711923 B1 | 4/2007 |
| KR | 1020100053297 A | 5/2010 |
| KR | 1020100122613 A | 11/2010 |
| KR | 101037135 B1 | 5/2011 |
| KR | 1020140069239 A | 6/2014 |
| KR | 1020140071574 A | 6/2014 |
| KR | 101430551 B1 | 8/2014 |
| KR | 1020150004146 A | 1/2015 |
| KR | 1020160061978 A | 6/2016 |

\* cited by examiner

METHOD OF PROCESSING SUBSTRATE AND METHOD OF FABRICATING SEMICONDUCTOR DEVICE USING THE SAME

CROSS-REFERENCE TO RELATED APPLICATIONS

This U.S. nonprovisional patent application claims priority under 35 U.S.C § 119 of Korean Patent Application No. 10-2017-0008219 filed on Jan. 17, 2017 entire contents of which are hereby incorporated by reference.

BACKGROUND

The described exemplary embodiments relates to a method of fabricating a semiconductor device, and more particularly, to a method of processing a substrate using a hardmask layer and a method of fabricating a semiconductor device using the method of processing a substrate.

A size of semiconductor chip becomes smaller with high levels of integration of the semiconductor chip. In general, the semiconductor device may be manufactured by unit processes such as a thin-film deposition process, a photolithography process, and an etching process. An inspection process may increase production yield by determining a normal or abnormal processing of the unit processes or by detecting defects in the manufactured semiconductor device.

SUMMARY

The disclosed exemplary embodiments provide a method of processing a substrate capable of increasing production yield and a method of fabricating a semiconductor device including the same.

According to exemplary embodiments of the inventive concept, a method of processing a substrate may include: forming a mask layer on a substrate; inspecting the mask layer; and forming a mask pattern based on an inspection result of the mask layer. The operation of inspecting the mask layer may comprise using Raman spectrum analysis to determine if there are defects in the mask layer.

According to exemplary embodiments of the inventive concept, a method of fabricating a semiconductor device may include: forming a hardmask layer on a substrate; detecting defects in the hardmask layer; determining whether the defects are outside of target patterns to be formed on the substrate; and removing the hardmask layer when at least one of the defects is present within the target patterns.

In one exemplary embodiment, there is a method of detecting defects in a semiconductor device, including: forming a hardmask on a substrate; emitting first light toward the hardmask; detecting second light scattered from the hardmask; determining whether there are defects in the hardmask, based on a first Raman peak of the second scattering light and a second Raman peak of the second scattering light, and determining positions of defects in the hardmask; determining whether the defects are in target patterns in the substrate, based on the positions of the defects; and etching the hardmask layer and the substrate to form patterns, the etching removing the defects.

DETAILED DESCRIPTION OF EXEMPLARY EMBODIMENTS

Figure 1:
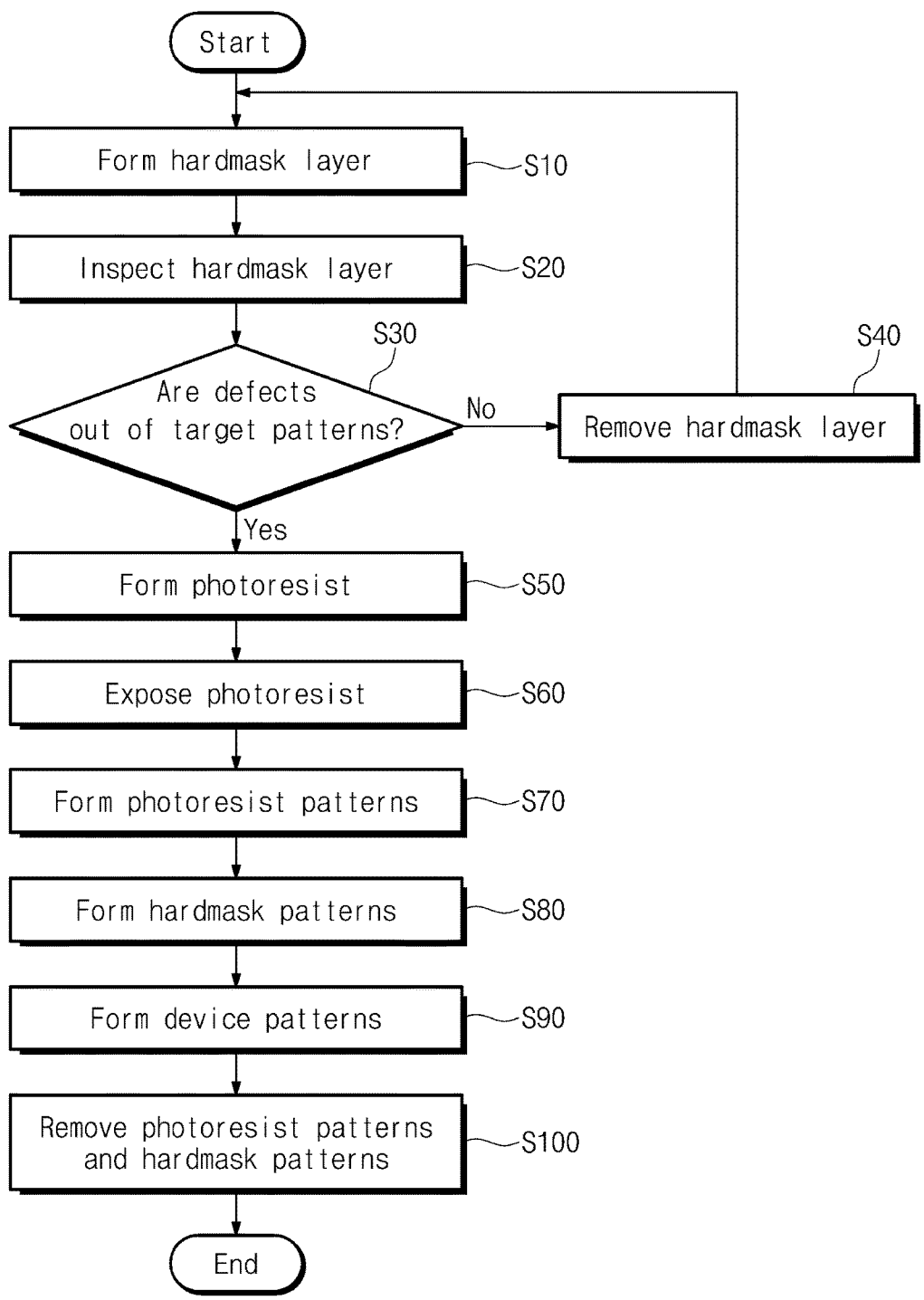
FIG. 1 is a flow chart illustrating a method of processing a substrate according to exemplary embodiments.

FIG. 1 is a flow chart illustrating a method of processing a substrate according to exemplary embodiments.

Referring to FIG. 1, a method of processing a substrate may include a method of fabricating a semiconductor device. Alternatively, the method of processing a substrate may include a method of fabricating a liquid crystal display (LCD) and/or an organic light emitting device (OLED) display. In an exemplary embodiment, the method of processing a substrate may include forming a hardmask layer (S 10), inspecting the hardmask layer (S20), determining whether defects are outside of target patterns (S 30), removing the hardmask layer (S 40), forming a photoresist (S 50), exposing the photoresist (S60), forming photoresist patterns (S70), forming hardmask patterns (S80), forming device patterns (S90), and removing the photoresist patterns and the hardmask patterns (S100). Operations S 10, S20, and S40 may be repeated as long as defects are found in the target patterns in operation S30. Once there are no defects in the target patterns, operations S50-S100 are performed.

FIGS. 2 to 9 are cross-sectional views sequentially illustrating the method of processing a substrate of FIG. 1.

Figure 2:
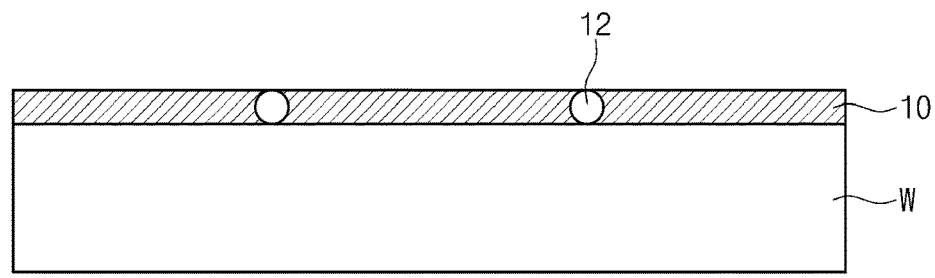
FIGS. 2 to 9 are cross-sectional views sequentially illustrating the method of processing a substrate of FIG. 1.

Referring to FIGS. 1 and 2, a hardmask layer 10, e.g., a mask layer, may be formed on a substrate W (S10). For example, the substrate W may include crystalline silicon. The substrate W may have a diameter of about 30 cm (in a planar direction perpendicular to the view of FIG. 2). The substrate W may include a semiconductor layer, an insulation layer, and/or a metal layer. Alternatively, the substrate W may include a glass substrate or a plastic substrate. In an exemplary embodiment, the hardmask layer 10 may include a polymer layer formed by a spin coating process and a baking process. For example, a source of the hardmask layer 10 may have a liquid state. The source of the hardmask layer 10 may be provided on a central portion of the substrate W. The substrate W may rotate at about 100 to about 2000 rpm in a spin coating process. The source of the hardmask layer 10 may be coated on an entire top surface of the substrate W. Thereafter, a baking process may be performed to solidify the hardmask layer 10.

In an exemplary embodiment, the hardmask layer 10 may have defects 12. For example, the defects 12 may include bubbles, pockets, irregularities, vacancies, surface irregularities, etc. Within the defects 12 there may be air, other gases, or materials which should not be present. In an exemplary embodiment, the defects 12 may be generated when the hardmask layer 10 is formed by the spin coating process and/or the baking process. The defects 12 may be caused by surface tension of the source of the hardmask layer 10, hydrophobicity of the top surface of the substrate W, and/or unevenness of the top surface of the substrate W. However, the generation of the defects 12 are not limited thereto and may arise for other reasons.

In an exemplary embodiment, the hardmask layer 10 may include pyrene, naphthalene, hydroxystyrene, and/or a surfactant. For example, the surfactant may include at least one from among dodecyltrimethylammonium bromide (DTMAB), miristyltrimethylammonium bromide (MTMAB), and cetyltrimethylammonium chloride (CTMAC). The surfactant may reduce occurrence of the defects 12 when the spin coating process is performed on the hardmask layer 10.

Figure 10:
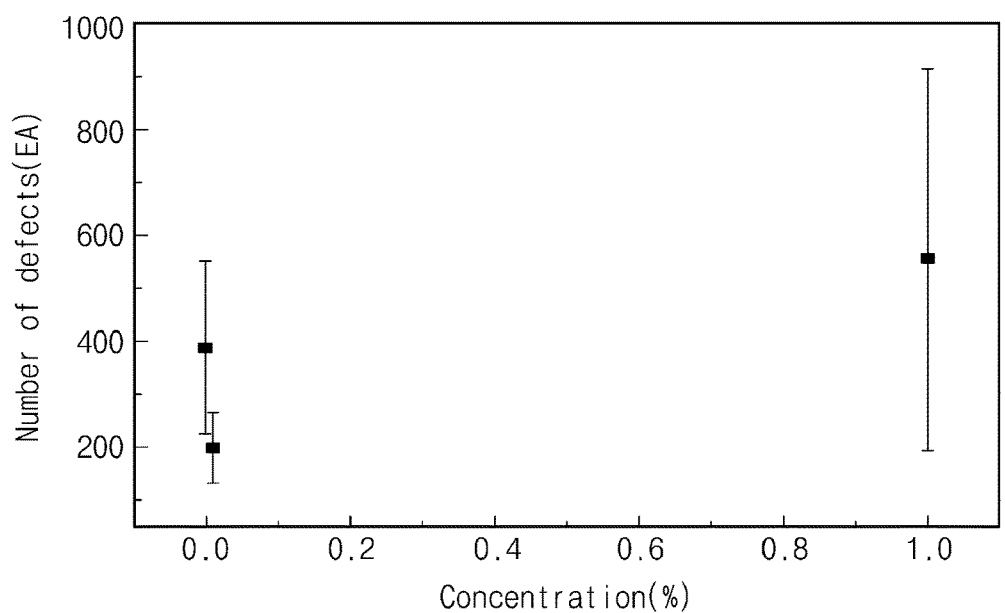
FIG. 10 is a graph illustrating how the number of defects depends on a surfactant concentration of a hardmask layer of FIG. 2.

FIG. 10 shows the number of the defects 12 depending on concentration of the surfactant included in the hardmask layer 10.

Referring to FIGS. 2 and 10, the number of the defects 12 may be dependent on concentration of the surfactant. For example, when the hardmask layer 10 was devoid of the surfactant, about 220 to about 550 defects 12 were detected. In this case, on average, about 400 defects 12 were detected. When the surfactant had concentration of about 1%, about 200 to about 900 defects 12 were detected. In this case, on average, about 600 defects 12 were detected. When the surfactant had concentration of about 0.03%, about 160 to about 250 defects 12 were detected. In this case, on average, about 200 defects 12 were detected. That is, when the surfactant of about 300 ppm is contained in the hardmask layer 10, the defects 12 may be detected at the lowest level. In this description, the unit "%" may be a weight %.

Figure 3:
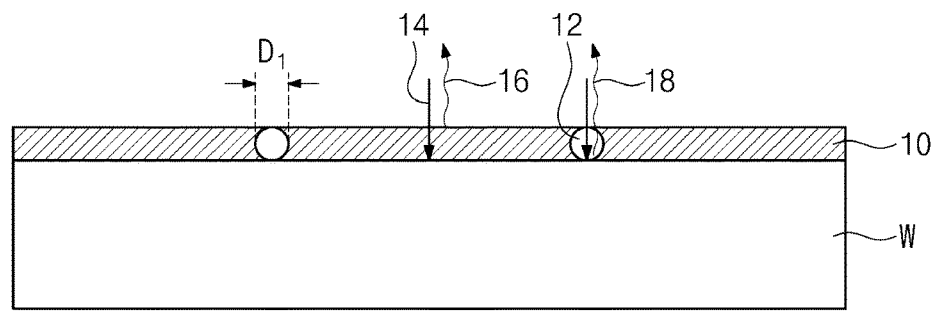
Figure 11:
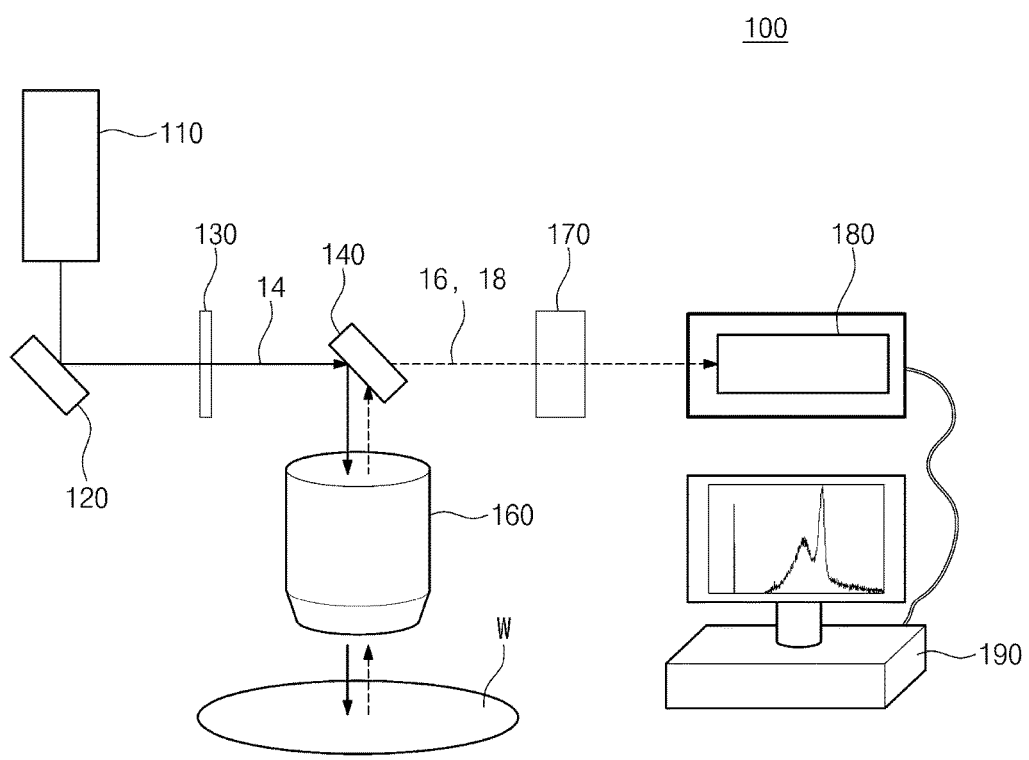
FIG. 11 is a schematic diagram illustrating an example of an inspection apparatus for inspecting a hardmask layer of FIG. 3.

FIG. 11 shows an example of an inspection apparatus 100 for inspecting the hardmask layer 10 of FIG. 3.

Referring to FIGS. 1, 3, and 11, the inspection apparatus 100 may inspect the hardmask layer 10 (S20) for detecting defects. In an exemplary embodiment, the inspection apparatus 100 may optically inspect the hardmask layer 10. For example, the inspection operation S20 of inspecting the hardmask layer 10 may include employing Raman spectrum analysis to detect the defects 12, i.e., to determine if there are defects 12. The inspection apparatus 100 may include a Raman spectrometer. Alternatively, the inspection apparatus 100 may include an optical microscope. The inspection apparatus 100 may electrically inspect the hardmask layer 10. For example, the inspection apparatus 100 may include an electron microscope.

Referring to FIGS. 3 and 11, when the inspection apparatus 100 provides light 14, e.g., first light, to the hardmask layer 10, a first scattering light 16 and/or a transmitted light, e.g., second light, may be generated from the hardmask layer 10. The first scattering light 16 may be an emitted light or light scattered from the hardmask layer 10. On the other hand, the defects 12 may generate a second scattering light 18. As the light 14 is provided to the substrate W after passing through the defects 12, the second scattering light 18 may be generated from the substrate W below the defects 12. Accordingly, the second scattering light 18 may be an emitted light from the substrate W. The inspection apparatus 100 may determine the defects 12 by comparing wavenumbers and/or wavelengths of the first scattering light 16 and the second scattering light 18, in an inspection result. For example, the inspection apparatus 100 may detect the defects 12 each of whose diameters is in the range of about 30 nm to about 1 mm.

Referring to FIG. 11, the inspection apparatus 100 may include a light source 110, a mirror 120, a filter 130, a beam splitter 140, an objective lens 160, a spectrometer 170, a detector 180, and a controller 190. The light source 110 may generate the light 14. The light 14 may include a laser beam. The mirror 120 may change a traveling path of the light 14 generated from the light source 110. The filter 130 may remove a noise in the light 14. The beam splitter 140 may provide the light 14 to the objective lens 160. The objective lens 160 may provide the light 14 to the substrate W. The first scattering light 16 and the second scattering light 18 may be generated from the hardmask layer 10 and the substrate W of FIG. 3. The objective lens 160 may provide the beam splitter 140 with the first scattering light 16 and the second scattering light 18. The beam splitter 140 may provide the spectrometer 170 with the first scattering light 16 and the second scattering light 18. The spectrometer 170 may split the first scattering light 16 and the second scattering light 18 based on their wavenumbers. The detector 180 may detect the first scattering light 16 that has been split or the second scattering light 18 that has been split. The controller 190 may determine the hardmask layer 10 or the defects 12 by using detection signals of the first scattering light 16 and the second scattering light 18 that have been detected. A stage (not shown) may be provided to horizontally move the substrate W. The controller 190 may detect the defects 12 in accordance with a position of the substrate W.

Figure 12:
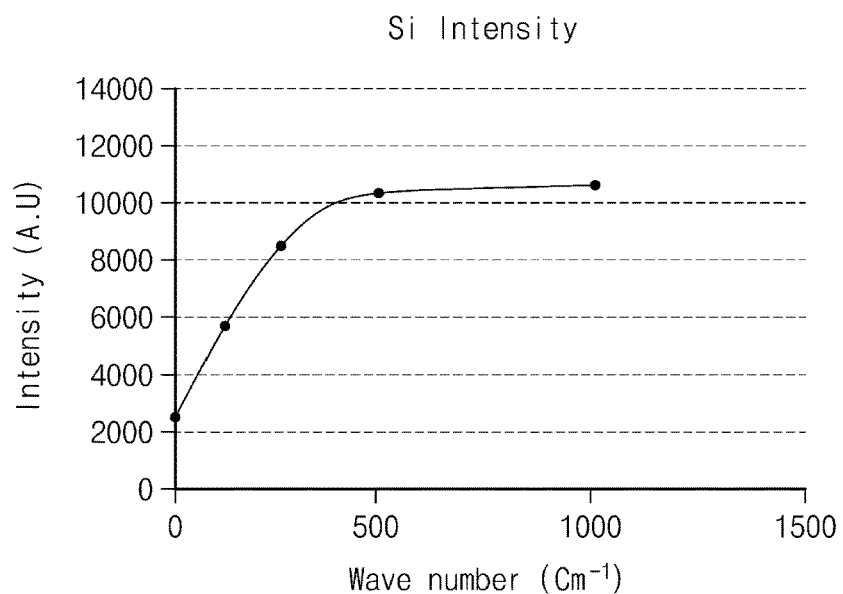
FIG. 12 is a graph illustrating intensity of a second scattering light versus wavenumber of light of FIG. 11.

FIG. 12 shows a detection intensity of the second scattering light 18 as a function of wavenumber of the light 14 of FIG. 11.

Referring to FIG. 12, when the light 14 has a wavenumber of more than about 400 $cm^{-1}$, the detection intensity of the second scattering light 18 may be almost saturated. Alternatively, when the wavenumber of the light 14 exceeds about 500 $cm^{-1}$, the first scattering light 16 and the second scattering light 18 of FIG. 3 may be reduced in their resolution. Accordingly, when the light 14 has a wavenumber of about 400 $cm^{-1}$ to about 500 $cm^{-1}$, the detection intensity and the resolution may be optimized. For example, the light 14 may have its wavenumber of about 402$cm^{-1}$.

Figure 13:
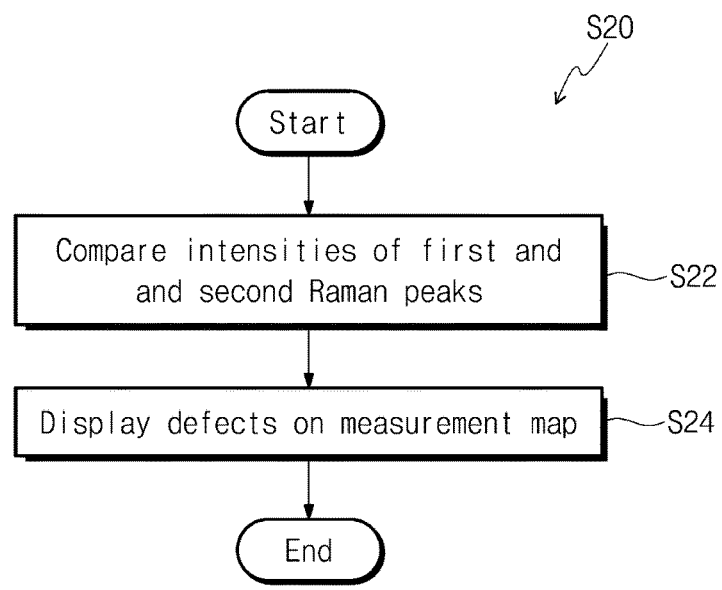
FIG. 13 is a flow chart exemplarily illustrating an inspection operation of inspecting a hardmask layer shown in FIG. 3.

FIG. 13 shows an example of the inspection operation S20 of inspecting the hardmask layer 10 shown in FIG. 3.

Referring to FIG. 13, the operation S20 of inspecting the hardmask layer 10 may include a operation S22 of comparing intensities of a first Raman peak and a second Raman peak and a operation S24 of displaying the defects 12 on a measurement map.

Figure 14:
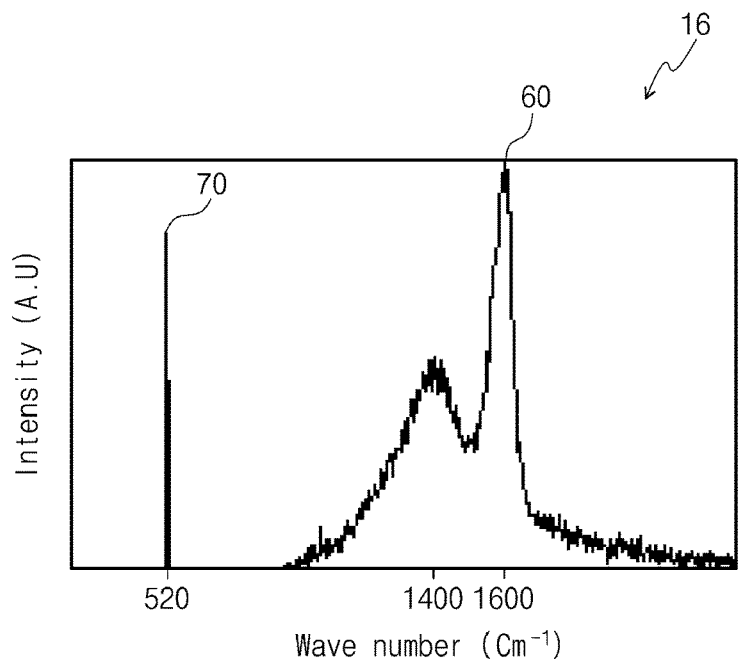
FIG. 14 is a graph illustrating first and second Raman peaks of a first scattering light shown in FIG. 3.
Figure 15:
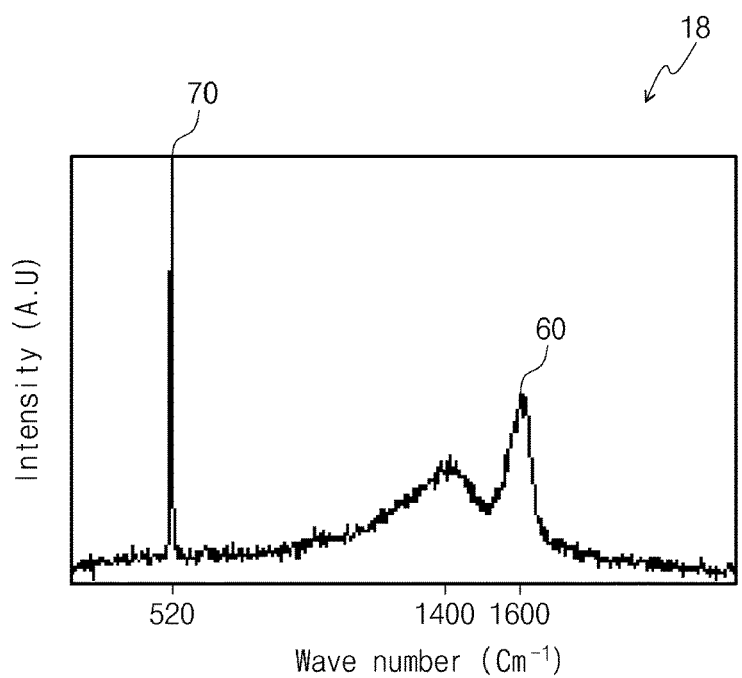
FIG. 15 is a graph illustrating first and second Raman peaks of a second scattering light shown in FIG. 3.

FIGS. 14 and 15 show a first Raman peak 60 and a second Raman peak 70 of each of the first scattering light 16 and the second scattering light 18 shown in FIG. 3, respectively.

Referring to FIGS. 11 and 13 to 15, the controller 190 may compare intensity of the first Raman peak 60 with intensity of the second Raman peak 70 to thereby determine whether the defects 12 are present (S22). In an exemplary embodiment, each of the first scattering light 16 and the second scattering light 18 may have the first Raman peak 60 and the second Raman peak 70. For example, the first Raman peak 60 may be obtained at a first wavenumber of about 1600$cm^{-1}$. The first Raman peak 60 with the first wavenumber of about 1600 $cm^{-1}$ may correspond to a G energy band of the hardmask layer 10. The second Raman peak 70 may be obtained at a second wavenumber of about 520 $cm^{-1}$. The second Raman peak 70 with the second wavenumber of about 520 cm$^{-1}$ may correspond to an energy band of the substrate W consisting of silicon. A peak with wavenumber of about 1400 cm$^{-1}$ between the first Raman peak 60 and the second Raman peak 70 may correspond to a D energy band of the hardmask layer 10. The peak with wavenumber of about 1400 cm$^{-1}$ may have intensity less than that of each of the first Raman peak 60 and the second Raman peak 70.

In an exemplary embodiment, at least one from among a first intensity of the first Raman peak and a first size of the first Raman peak may be compared with at least one from among a second intensity of the second Raman peak and a second size of the second Raman peak. Specifically, the controller 190 may compare intensity and/or size of the first Raman peak 60 with intensity and/or size of the second Raman peak 70 to thereby determine detections of the first scattering light 16 and the second scattering light 18. In addition, based on intensities and/or sizes of the first Raman peak 60 and the second Raman peak 70, the controller 190 may determine detection of one of the hardmask layer 10 and the defects 12.

Referring to FIG. 14, the first Raman peak 60 of the first scattering light 16 may be higher than the second Raman peak 70 of the first scattering light 16. For example, when the first Raman peak 60 is higher than the second Raman peak 70, the controller 190 may determine that the first scattering light 16 and/or the hardmask layer 10 are detected. The controller 190 may also determine that no defects 12 are present in the hardmask layer 10.

Referring to FIG. 15, the first Raman peak 60 of the second scattering light 18 may be lower than the second Raman peak 70 of the second scattering light 18. For example, when the second Raman peak 70 is higher than the first Raman peak 60, the controller 190 may determine that the second scattering light 18 and/or the substrate W are detected. The controller 190 may also determine that the defects 12 are present in the hardmask layer 10.

In addition, the controller 190 may determine sizes of the defects 12 based on a difference in intensity of the first Raman peak 60 and the second Raman peak 70. For example, the sizes of the defects 12 may increase in proportion to intensities of the first Raman peak 60 and the second Raman peak 70.

Figure 16:
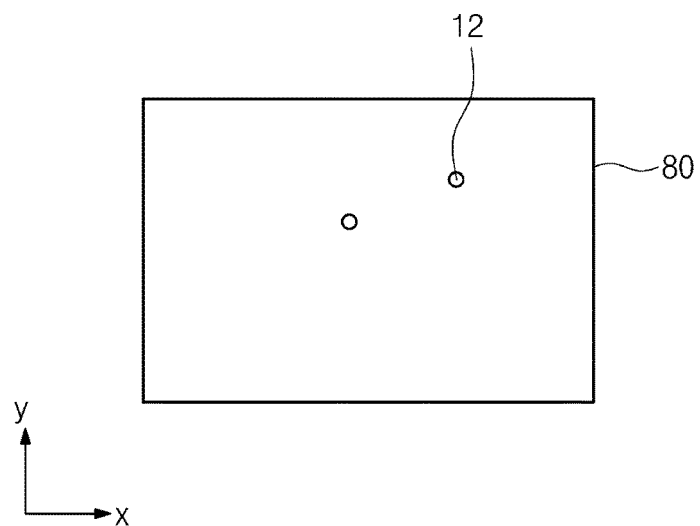
FIG. 16 is a plan view illustrating a measurement map of defects shown in FIG. 3.

FIG. 16 shows a measurement map 80 of the defects 12 shown in FIG. 3.

Referring to FIGS. 11, 13, and 16, the controller 190 may indicate the defects 12 on the measurement map 80 in accordance with a position of the substrate W (S24). For example, the measurement map 80 may display the defects 12 in an x-y coordinate system. The measurement map 80 may also display sizes of the defects 12. The controller 190 may manage the defects 12 based on their positions and sizes on the measurement map 80.

Figure 17:
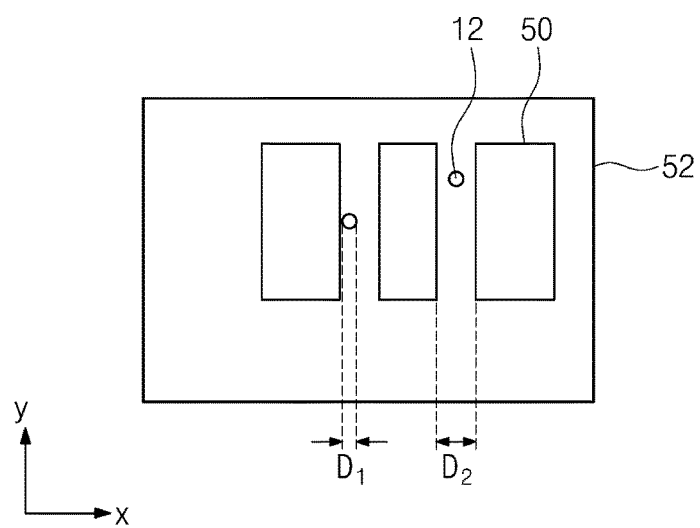
FIG. 17 is a plan view illustrating target patterns comparative to defects of FIG. 16.

FIG. 17 shows target patterns 50 comparative to the defects 12 of FIG. 16.

Referring to FIGS. 1, 11, and 17, the controller 190 may determine whether the defects 12 are outside of the target patterns 50 (S30). The target patterns 50 may be disposed on a target map 52, i.e., an exposure map. The target map 52 may be overlapping with the measurement map 80 of FIG. 16. The defects 12 may be compared with the target patterns 50. In an exemplary embodiment, the target patterns 50 may be spaced apart from each other at a distance based on a size of the defects 12. For example, the target patterns 50 may be spaced apart from each other at a distance D2 that is greater than a diameter D1 of one of the defects 12. For example, when the diameter D1 of one of the defects 12 is about 30 nm, the distance D2 between target patterns 50 that are neighboring may be greater than about 30 nm.

When the defects 12 are disposed within the target patterns 50, the hardmask layer 10 may be removed (S40). This may be because that the defects 12 may cause failure of the operation S90 of forming subsequent device patterns. Thereafter, an iteration may be performed to carry out the operation S10 of forming the hardmask layer 10 through the operation S30 of determining whether the defects 12 are outside of the target patterns 50.

Figure 4:
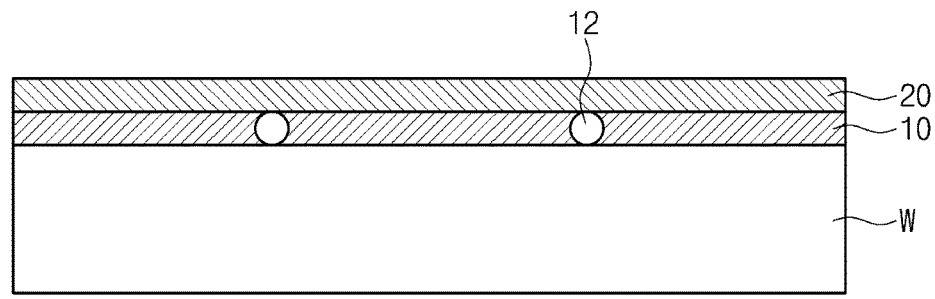

FIGS. 1 and 4, when the defects 12 are disposed outside the target patterns 50, a photoresist 20 may be formed on the hardmask layer 10 (S50). The photoresist 20 may be used as an etch mask to etch the hardmask layer 10 in a subsequent process. For example, a spin coating process may be employed to coat the photoresist 20. The photoresist 20 may have benzene chains.

Figure 5:
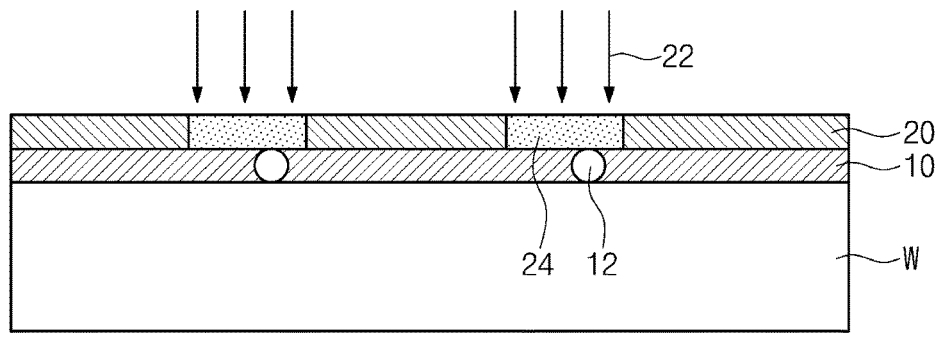

Referring to FIGS. 1 and 5, the photoresist 20 may be exposed to an ultraviolet light 22 (S60). For example, a source (not shown) of the ultraviolet light 22 may include extreme ultraviolet (EUV) light having a wavelength of about 10 nm, argon fluoride (ArF) having a wavelength of about 193 nm, krypton fluoride (KrF) having a wavelength of about 248 nm, i-line having a wavelength of about 365 nm, or g-line having a wavelength of about 436 nm. The ultraviolet light 22 may break benzene chains in a portion 24 of the photoresist 20. The photoresist 20 may be provided with the ultraviolet light 22 along the target map 52 of FIG. 17. The target map 52 may include a revised map that is modified based on a wavelength of the ultraviolet light 22 and/or arrangement of the target patterns 50. The ultraviolet light 22 may be provided onto the photoresist 20 on the defects 12.

Figure 6:
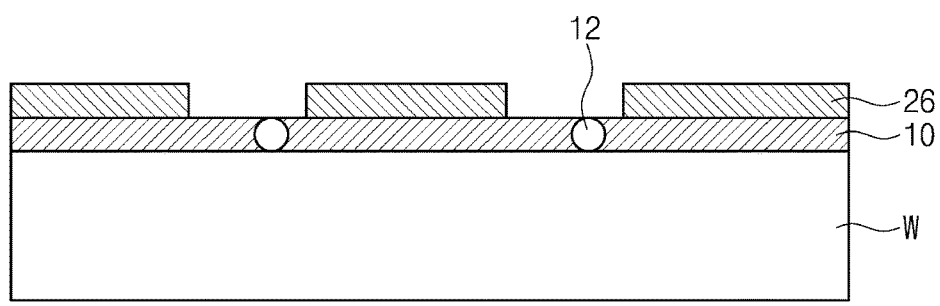

Referring to FIGS. 1 and 6, the photoresist 20 that has been exposed, i.e., exposed photoresist, may be developed to form photoresist patterns 26 (S70), i.e., developing the exposed photoresist to form a photoresist pattern is performed. A development solution (not shown) may remove the portion 24 of the photoresist 20 that has been exposed. The photoresist patterns 26 may reveal the defects 12 of the hardmask layer 10.

Figure 7:
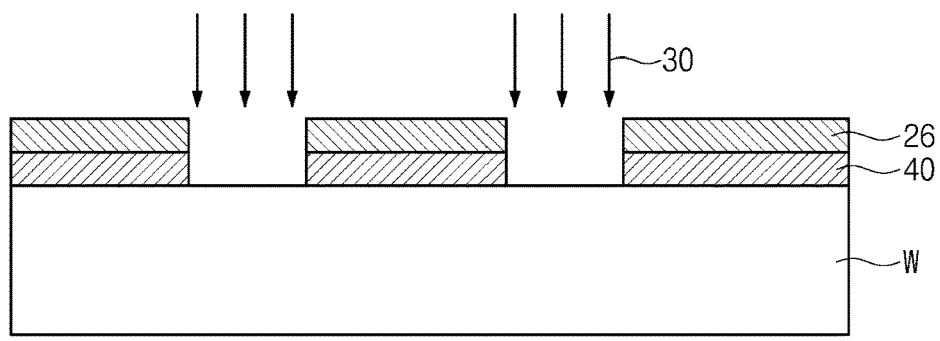

Referring to FIGS. 1 and 7, hardmask patterns 40 may be formed by removing portions of the hardmask layer 10 that are revealed and/or exposed through the photoresist patterns 26 (S80). The photoresist patterns 26 may be used as an etch mask to etch the hardmask layer 10. In an exemplary embodiment, a dry etching process may be employed to remove the hardmask layer 10. For example, the dry etching process may use an etching gas 30 including CF3 or CF4. The defects 12 may be removed. A plasma may be used to cause the etching gas 30 to accelerate and/or concentrate on the substrate W.

Figure 8:
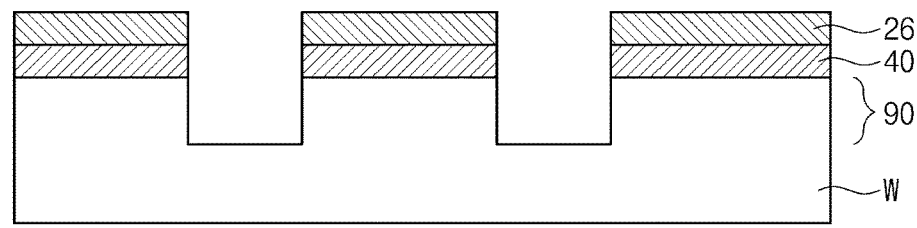

Referring to FIGS. 1 and 8, device patterns 90 may be formed by removing portions of the substrate W that are exposed through the photoresist patterns 26 and the hardmask patterns 40 (S90). The device patterns 90 may be formed along the photoresist patterns 26 and the hardmask patterns 40. In an exemplary embodiment, the device patterns 90 may correspond to the target patterns 50 of FIG. 17. No defects 12 of FIG. 2 may be found in the hardmask patterns 40 on the device patterns 90. Alternatively, the target patterns 50 may be reference patterns and/or etch correction patterns of the device patterns 90.

At least a portion of the substrate W may be in-situ removed together with the hardmask layer 10. A dry etching process may remove the at least a portion of the substrate W. For example, the dry etching process of the substrate W may use an etching gas (not shown) including $SF_6$, HF, HCl, $H_2SO_4$, $HNO_3$, $H_3PO_4$, $NH_4$, $(NH_4)_2SO_5$, $NH_4Cl$, $CF_3$, $CF_4$, or any combination thereof. Ones of the photoresist patterns 26 and the hardmask patterns 40 may be partially damaged and/or removed when the substrate W is etched. For example, when the defects 12 remain in the hardmask patterns 40, the device patterns 90 may suffer from failure. According to the inventive concept, as the hardmask patterns 40 have no defects 12, no failure may occur in the substrate etching process. The device patterns 90 may be formed without etching failure. It thus may be possible to increase production yield.

Figure 9:
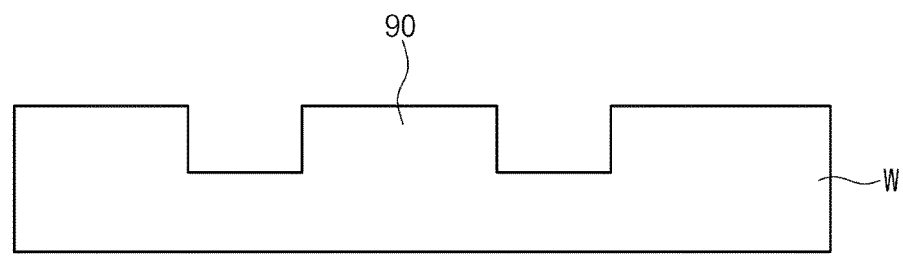

Referring to FIGS. 1 and 9, the photoresist patterns 26 and the hardmask patterns 40 may be removed (S100). For example, an ashing process may be carried out to remove the photoresist patterns 26 and the hardmask patterns 40. Alternatively, an organic solvent may be used to remove the photoresist patterns 26 and the hardmask patterns 40.

As discussed above, a method of processing a substrate according to embodiments of the inventive concept may include detecting defects such as bubbles in the hardmask layer and determining whether the defects are outside of the target patterns. The defects may be detected by Raman spectrum analysis. When it is determined that the defects are present within the target patterns, the hardmask layer may be removed and then newly formed on the substrate. The substrate etching process may be prevented from failure caused by the defects, and production yield may be increased.

Although the present invention has been described in connection with the embodiments of the present invention illustrated in the accompanying drawings, it will be understood to those skilled in the art that various changes and modifications may be made without departing from the technical spirit and essential feature of the present invention. It therefore will be understood that the embodiments described above are just illustrative but not limitative in all aspects.

What is claimed is:

1. A method of processing a substrate, comprising:
   forming a mask layer on the substrate having an etched region and a non-etched region defined by the etched region;
   inspecting the mask layer to detect defects in the mask layer using Raman spectrum analysis;
   determining whether the defects are on the etched region or the non-etched region if the defects are in the mask layer;
   removing the mask layer on the etched region and the non-etched region of the substrate if the defects are on the non-etched region; and
   etching a portion of the mask layer on the etched region to form a mask pattern on the non-etched region if the defects are on the etched region.

2. The method of processing the substrate of claim 1, wherein the defects comprise bubbles in the mask layer.

3. The method of processing the substrate of claim 1, wherein the inspecting the mask layer further comprises comparing a first Raman peak with a second Raman peak of each of the mask layer and the substrate,
   wherein the defects are detected in the mask layer when the first Raman peak is lower than the second Raman peak.

4. The method of processing the substrate of claim 3, wherein the first Raman peak is obtained at a first wavenumber of about 1600 $cm^{-1}$, and the second Raman peak is obtained at a second wavenumber of about 520 $cm^{-1}$.

5. The method of processing the substrate of claim 1, wherein inspecting the mask layer further comprises displaying the defects on a measurement map.

6. The method of processing the substrate of claim 1, wherein etching a portion of the mask layer on the etched region comprises:
   forming a photoresist on the mask layer;
   exposing a portion of the photoresist on the etched region;
   developing the photoresist that has been exposed, to form a photoresist pattern on the non-etched region; and
   removing the portion of the mask layer on the etched region using the photoresist pattern.

7. The method of processing the substrate of claim 1, wherein the mask layer comprises at least one from among pyrene, naphthalene, hydroxystyrene, and a surfactant,
   wherein the surfactant has concentration of about 0.03%.

8. A method of fabricating a semiconductor device, comprising:
   forming a hardmask layer on a substrate having an etched region and a non-etched region defined by the etched region;
   detecting defects in the hardmask layer;
   determining whether the defects are on the etched region or the non-etched region if the defects are in the hardmask layer;
   determining whether the defects are on the etched region or the non-etched region if the defects are in the mask layer;
   removing the hardmask layer on the etched region and the non-etched region of the substrate if the defects are on the non-etched region; and
   etching a portion of the hardmask layer on the etched region to form a mask pattern on the non-etched region if the defects are on the etched region.

9. The method of fabricating a semiconductor device of claim 8, wherein detecting the defects in the hardmask layer comprises using Raman spectrum analysis.

10. The method of fabricating a semiconductor device of claim 8, wherein the defects comprise bubbles in the hardmask layer.

11. The method of fabricating a semiconductor device of claim 8, wherein, when the defects each have a diameter of about 30 nm, the target patterns are formed to be spaced apart from each other at a distance of more than about 30 nm.

12. The method of fabricating a semiconductor device of claim 8, wherein etching a portion of the mask layer on the etched region comprises:
   forming a photoresist on the hardmask layer;
   exposing a portion of the photoresist on the etched region;
   developing the photoresist to form photoresist patterns on the non-etched region; and
   removing the portion of the hardmask layer and a portion of the substrate along the photoresist patterns to form hardmask patterns and device patterns.

13. A method of detecting defects in a semiconductor device, comprising:
   forming a hardmask layer on a substrate;
   emitting a first light toward the hardmask layer;
   detecting a second light scattered from the hardmask layer;
   determining whether there are defects in the hardmask layer, based on a first Raman peak of the second light and a second Raman peak of the second light, and determining positions of defects in the hardmask layer;

determining whether the defects are on the etched region or the non-etched region if the defects are in the hardmask layer;

removing the hardmask layer on the etched region and the non-etched region of the substrate if the defects are on the non-etched region; and etching a portion of the hardmask layer on the etched region to form a mask pattern on the non-etched region if the defects are on the etched region.

14. The method of detecting defects in the semiconductor device of claim 13, wherein the forming the hardmask layer on the substrate comprises forming a polymer layer formed by spin coating and baking a source in a liquid state, and wherein the hardmask layer comprises the defects.

15. The method of detecting defects in the semiconductor device of claim 13, wherein the defects comprises at least one from among bubbles, pockets, and vacancies.

16. The method of detecting defects in the semiconductor device of claim 13, wherein the determining whether the defects are in the hardmask layer comprises comparing at least one from among a first intensity of the first Raman peak and a first size of the first Raman peak with at least one from among a second intensity of the second Raman peak and a second size of the second Raman peak.

\* \* \* \* \*